United States Patent [19]

Sikorski et al.

[11] 4,407,764

[45] Oct. 4, 1983

[54] N-ARYLSULFINYL N-PHOSPHONOMETHYLGLYCINONITRILES

[75] Inventors: James A. Sikorski, West Lafayette, Ind.; Mary A. Hoobler, Creve Coeur, Mo.

[73] Assignee: Monsanto Company, St. Louis, Mo.

[21] Appl. No.: 298,056

[22] Filed: Aug. 31, 1981

[51] Int. Cl.³ .................. C07F 9/40; A01N 57/20
[52] U.S. Cl. ........................ 260/940; 71/86; 260/969
[58] Field of Search ............. 260/940; 71/87

[56] References Cited

U.S. PATENT DOCUMENTS 4,176,225 11/1979 Sturtz et al. .................. 260/940
4,252,554 2/1981 Dutra et al. .................. 71/87
4,300,943 11/1981 Dutra et al. .................. 71/87

*Primary Examiner*—Anton H. Sutto
*Attorney, Agent, or Firm*—G. F. Sieckmann; R. C. Loyer

[57] ABSTRACT

Ester derivatives of N-arylsulfinyl-N-phosphonomethylglycinonitriles useful as herbicides. Also described is a process for preparing the same, herbicidal compositions containing the same, and herbicidal methods employing such glycinonitriles and herbicidal compositions.

6 Claims, No Drawings

N-ARYLSULFINYL N-PHOSPHONOMETHYLGLYCINONITRILES

This invention relates to novel ester derivatives of N-arylsulfinyl-N-phosphonomethylglycinonitrile which are useful as herbicides. This invention further relates, a process for preparing the same, to herbicidal compositions containing such N-phosphonomethyl-glycinonitriles and to herbicidal methods employing such compounds and compositions.

U.S. Pat. No. 4,067,719 issued to Gerard A. Dutra on Jan. 10, 1978 discloses N-phosphonomethylglycinonitriles of the formula

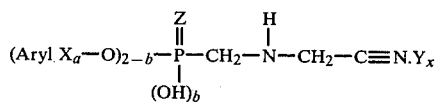

wherein (Aryl) is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 2, provided that x must be zero when b is 1, as well as a process for producing such compounds. These N-phosphonomethylglycinonitriles are said to be useful as herbicides.

U.S. Pat. No. 4,008,296 issued to John Edward D. Barton on Feb. 15, 1977 describes ester derivatives of N-phosphonomethylglycinonitrile having the formula

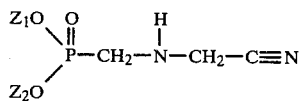

wherein $Z_1$ and $Z_2$ each represent an alkyl radical of from 1 to 6 carbon atoms; which are said to be useful as herbicides.

U.S. Pat. No. 4,252,554 issued to Gerard A. Dutra et al. on Feb. 24, 1981 discloses compounds represented by the formula

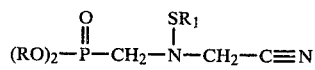

wherein R is phenyl, naphthyl or biphenylyl or phenyl, naphthyl or biphenylyl substituted with from 1 to 3 substituents independently selected from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from 1 to 3 substituents independently selected from the class consisting of lower alkyl, lower alkoxy, halogen, trifluoromethyl and nitro.

The compounds of the present invention are represented by the formula

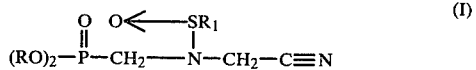

wherein R is selected from the group consisting of phenyl, naphthyl, biphenylyl; or phenyl, naphthyl or biphenylyl substituted with from 1 to 3 substituents independently selected from the class consisting of hydrogen, lower alkyl, lower alkoxy and methylenedioxy and $R_1$ is phenyl or phenyl substituted with from 1 to 3 substituents selected from the group consisting of lower alkyl and lower alkoxy.

Illustrative of the substituted phenyl groups which R represents are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethyl-phenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethyl-thio)phenyl, trimethylphenyl, trichlorophenyl, tributylphenyl, ethyldichlorophenyl and the like.

Groups representative of a substituted naphthyl group include methylnaphthyl, nitronaphthyl, bromonaphthyl, dimethyl naphthyl, difluoro naphthyl, trimethylnaphthyl and the like.

Groups representative of substituted biphenylyl groups represented by R include methyl-biphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have from 1 to 4 carbon atoms in a straight or branched chain, such as, for example, methyl, ethyl, propyl, isopropyl, butyl, isobutyl, sec-butyl, and t-butyl.

In a preferred embodiment, R is phenyl, or phenyl substituted with one group comprising lower alkoxy or lower alkyl and $R_1$ is independently phenyl or phenyl substituted with one group comprising lower alkyl or lower alkoxy.

R is phenyl or methoxyphenyl and $R_1$ is independently phenyl or methylphenyl.

In accordance with the present invention, N-phosphonomethylglycinonitriles of formula (I) are prepared by reacting a compound of the formula

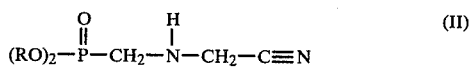

wherein R is as above defined; in an aprotic solvent, with aryl sulfinyl chloride of the formula

wherein $R_1$ is as above defined; in the presence of a hydrogen chloride acceptor and at a reaction temperature which is necessary to initiate and sustain the aforedescribed reaction, typically in the range from about 0° to about 100° C. However, for ease of reaction and recovery of product, it is preferred to conduct the process of the present invention within a range of about 10° to about 50° C.

In preparing the novel glycinonitriles of formula (I), the ratio of reactants is not narrowly critical. For best results, however, for each mole of a compound of formula (II), one should employ one mole of a sulfinyl chloride of formula (III) to produce one mole of a glycinonitrile compound of formula (I). It is preferred to employ an excess of aryl sulfinyl chloride of formula (III) for ease of reaction and maximum yield of product. The hydrogen chloride acceptor is preferably used in stoichiometric excess to insure completeness of reaction.

The hydrogen chloride acceptor is typically an amine, preferably a tertiary amine, which is inert with the reactants employed or products formed. Examples of acceptable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the acceptable aprotic solvents which may be employed in the process of this invention include methylene chloride, benzene, toluene, tetrahydrofuran, cyclohexane, methylcyclohexane, hexane, octane, dioxane, ethyl ether, mixtures thereof and the like.

While the process of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

In the following examples the particular aryl sulfinyl chloride employed as a reactant in Example 1, e.g., p-toluene sulfinyl chloride was prepared by generally following a method particularly described in Org. Syn. Coll. Vol. IV, pp. 937–939 (1963) Frederick Kurzer which is incorporated herein in its entirety.

This method is based on the reaction of thionyl chloride with powdered sodium p-toluene sulfinate dihydrate to yield initially a clear yellow liquid containing a white opaque solid. Excess thionyl chloride is removed by vacuum distillation. The crude sulfinyl chloride solvent is treated with anhydrous ether and a subsequent distillation leaves the sulfinyl chloride as a clear pale straw-yellow oil.

Aryl sulfinyl chloride employable as a reactant, may be prepared in a superior fashion by generally following a method described in "A Superior Method For Preparing Sulfinyl Chlorides," Journal of Organic Chemistry, Vol. 33, pp. 2104–2108 (1968), Irwin B. Douglass and Richard V. Norton which is incorporated herein in its entirety by reference. The aforementioned method is based on chlorination of a mixture of alkyl or aryl disulfide and acetic anhydride to yield the desired arylsulfinyl chloride and acetyl chloride.

Preparation of p-Toluene Sulfinyl Chloride

In connection with the aforedescribed Douglass and Norton method, preparation of p-toluene sulfinyl chloride was accomplished. In an oven-dried 250 ml sidearm round bottom flask with magnetic stirring bar and a stopcock connector by slurring 24.6 g (0.1 mol) of freshly recrystallized p-tolyldisulfide in 18.8 ml (0.2 mol) of distilled acetic anhydride. The resulting mixture was cooled to $-10$ to $-20°$ C. in a water-ethylene glycol-dry ice bath. All transfers and reactions occured under nitrogen blanket. About 7 ml of chlorine was condensed at $-78°$ C. and transferred by cannula over 15 minutes to the reaction composition. The reaction became a clear bright orange solution and then the orange color began to fade. Additional chlorine was added in 1 ml portions until the solution turned to a greenish-yellow color. The solution was stirred at $-10°$ C. for 1 hour and acetylchloride was distilled off under reduced pressure employing a water aspirator while allowing the solution to return to room temperature. The bubbling ceased after about 45 minutes and the solution was hooked to a vacuum pump for $\frac{1}{2}$ hour at room temperature and then heated to about 40° C. under vacuum for 20 minutes to yield 34.5 g of a green liquid. Thereafter 34.43 g were diluted into a 50 ml solution in toluene and stored under a nitrogen blanket for further use.

EXAMPLE 1

To a solution of [[[cyanomethyl]amino]methyl] phosphonic acid, diphenyl ester (9.0 g, 0.03 mol) and triethylamine (3.0 g, 0.03 mole) in toluene at 15° C. was added dropwise via syringe p-toluenesulfinyl chloride (5.2 g, 0.03 mol) prepared in a manner as described above. The yellow reaction mixture was allowed to gradually warm to room temperature over a 6 hour period. A precipitate of triethylamine hydrochloride was removed by filtration. The toluene filtrate was washed with cold 10% aqueous sodium hydroxide and cold water, dried over magnesium sulfate, filtered, and then concentrated on a rotovap to give 12.8 g of a yellow oil. This oil was then adsorbed onto silica gel and purified by high pressure liquid chromatography (HPLC) on a $1'' \times 4'$ silica gel column to give the desired product, phosphonic acid, [[(cyanomethyl) [(4-methylphenyl)-sulfinyl]amino]methyl], diphenyl ester, as a yellow oil, 1.2 g (10%) which slowly crystallized on standing to give a white solid, m.p. 75°–77° C., corresponding to a compound of formula (I) wherein R is phenyl and $R_1$ is 4-methylphenyl.

Analysis Calculated for $C_{22}H_{21}N_2O_4P_1S_1$: C, 59.99; H, 4.81; N, 6.36; S, 7.28. Found: C, 59.25; H, 5.08; N, 6.21; S, 7.06.

Preparation of Benzene Sulfinyl Chloride

In an oven dried 250 ml sidearm round bottom flask, prepared by following the Douglass and Norton method 21.8 g (0.1 mol) of freshly recrystallized phenyl disulfide was slurried in 18.8 ml (0.2 mol) of distilled acetic anhydride. The resulting mixture was cooled to $-10°$ C. in a dry ice-water-ethylene glycol bath. To it was added over a 10 hour period 8 ml of liquid chlorine. The reaction became a clear organe solution which was stirred for 15 minutes. Additional liquid chlorine was added in 1 ml portions until the solution turned to a greenish-yellow color. The solution was stirred at $-10°$ C. for $1\frac{1}{2}$ hours. The total amount of liquid chlorine added was about 15 ml. The solution was removed from the bath and hooked to a water aspirator as the flask warmed to room temperature. When bubbling of the solution had ceased, the flask was hooked to a vacuum pump for ½ hour at room temperature and then the temperature was increased to 40° C. for about another ½ hour. The flask was removed from the vacuum pump and the yellow contents of the flask were found to weigh 31.8 g. The contents were placed under vacuum at 40° C. for an additional 20 minutes to give 31.75 g (95%) brown liquid. This material was dissolved in toluene and diluted to 50 ml of solution for later use.

General Preparation of Examples 2 and 3

The appropriate neutral glyphosate (0.03 mol) was dissolved in 150 ml of toluene in an oven-dried 250 mL flask that had been cooled under nitrogen. Triethylamine (0.03 mol) was then added. A solution of benzenesulfinyl chloride in toluene was then slowly added dropwise via syringe. When the addition was complete, the reaction mixture was stirred at room temperature overnight. A $^{31}$P NMR indicated complete uptake of starting material. The precipitate of triethylamine hydrochloride was removed by filtration. The toluene filtrate was adsorbed onto silica gel and purified by HPLC on a 1"×4' silica gel column to give the desired glyphoste sulfinamides. $^1$H and $^{31}$P NMR, FDMS, and elemental analysis were all consistent with pure material.

EXAMPLE 2

In Example 2, phosphonic acid, [[(cyanomethyl) (phenyl sulfinyl)amino]methyl], diphenyl ester was prepared as a glyphosate sulfinamide (white solid) in 45% yield corresponding to a compound of formula (I) wherein R and $R_1$ are both phenyl, having a melting point of 63°–70° C. which employed Phosphonic acid,-[[(cyanomethyl)amino]methyl], diphenyl ester, as a glyphosate reactant.

Analysis Calculated: C, 59.15; H, 4.49; N, 6.57; S, 7.52; Found: C, 59.19; H, 4.52; N, 6.58; S, 7.54.

EXAMPLE 3

In Example 3, phosphonic acid, [[(cyanomethyl) (phenyl sulfinyl)amino]methyl],bis (2-methoxyphenyl)ester was prepared as a glyphosate sulfinamide (yellow oil) corresponding to a compound of formula (I) wherein R is 2-methoxyphenyl and $R_1$ is phenyl, which employed Phosphonic acid, [[(cyanomethyl-)amino]methyl], bis(2-methoxyphenyl) ester as a glyphosate reactant.

Analysis Calculated: C, 56.79; H, 4.77; N, 5.76; S, 6.59; Found: C, 56.55; H, 4.80; N, 5.70; S, 6.50.

EXAMPLE 4

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A—Canada Thistle* | K—Barnyardgrass |
| B—Cocklebur | L—Soybean |
| C—Velvetleaf | M—Sugar Beet |
| D—Morningglory | N—Wheat |
| E—Lambsquarters | O—Rice |
| F—Smartweed | P—Sorghum |
| G—Yellow Nutsedge* | Q—Wild Buckwheat |
| H—Quackgrass* | R—Hemp Sesbania |
| I—Johnsongrass* | S—Panicum Spp |
| J—Downy Brome | T—Crabgrass |

*Established from vegetative propagules.
A dash (—) in the tables indicates that the particular species was absent in the test.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 4 | 4 | 4 | 3 | 4 | 2 | 2 | 2 | 2 | 3 | 3 |
|   | 4 | 5.6 | 2 | 3 | 3 | 2 | 3 | 1 | 2 | 1 | 3 | 2 | 2 |
| 2 | 4 | 11.2 | 2 | 2 | 2 | 2 | 4 | 0 | 2 | 1 | 3 | 1 | 3 |
|   | 4 | 5.6 | 2 | 2 | 2 | 2 | 4 | 0 | 2 | 1 | 3 | 1 | 2 |
| 3 | 4 | 11.2 | 2 | 3 | 1 | 2 | 4 | 1 | 2 | 0 | 2 | 0 | 1 |

TABLE I-continued

| Compound of Example No. | WAT | kg/h | A | B | C | D | E | F | G | H | I | J | K |
|---|---|---|---|---|---|---|---|---|---|---|---|---|---|
| | 4 | 5.6 | 2 | 2 | 1 | 2 | 3 | 1 | 1 | 2 | 3 | 1 | 2 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 2 | 1 | 1 | 1 | 3 | 3 | 2 | 2 | 1 | 4 | 1 | 1 | 2 | 3 | 3 | 4 |
| | 4 | 1.12 | 1 | 1 | 0 | 1 | 2 | 1 | 0 | 1 | 0 | 4 | 2 | 0 | 0 | 0 | 1 | 3 |
| | 2 | 0.28 | 0 | 0 | 0 | 0 | 0 | 0 | 1 | 0 | 0 | 1 | 0 | 0 | 0 | 0 | 0 | 1 |
| | 2 | 0.06 | 0 | 0 | 0 | 0 | 0 | 0 | 0 | 0 | 0 | 1 | — | 0 | 0 | 0 | 0 | — |
| 2 | 4 | 5.6 | 2 | 1 | 1 | 2 | 3 | 3 | 2 | 2 | 4 | 4 | — | 2 | 2 | 3 | 3 | 3 |
| | 4 | 1.12 | 1 | 0 | 0 | 0 | 3 | 2 | 0 | 2 | 1 | 2 | 1 | 1 | 0 | 0 | 2 | 3 |
| | 2 | 0.28 | 0 | 0 | 0 | 0 | 1 | 1 | 0 | 1 | 0 | 1 | 0 | 0 | 0 | 0 | 1 | 2 |
| 3 | 4 | 5.6 | 2 | 2 | 1 | 2 | 3 | 3 | 2 | 2 | 1 | 3 | 2 | 1 | 1 | 2 | 2 | 3 |
| | 4 | 1.12 | 1 | 0 | 0 | 1 | 2 | 2 | 1 | 2 | 1 | 3 | 2 | 1 | 1 | 1 | 2 | 3 |
| | 2 | 0.28 | 0 | 0 | 0 | 0 | 1 | 1 | 0 | 1 | 0 | 3 | 0 | 0 | 0 | 0 | 0 | 2 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing gents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene dreivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulphonate, polymethylene bisnaphthalenesulfonate and sodium N-methyl-N-(long chain acid) taurates.

The following list gives some specific herbicidal compositions of this invention. While the compositions hereinafter listed have not been actually prepared, the compositions are provided since it is believed that they are within the inventive concept.

| | | |
|---|---|---|
| 1. | Phosphonic Acid, [[(cyano-methyl)][(4-methylphenyl)sulfinyl] amino]methyl]-,diphenyl ester | 25 parts |
| | Aerosol OTB | 4 parts |
| | Lignosulfonate | 2 parts |
| | Kaolinite clay | 65 parts |
| | The components are blended and ground to give a fine, wettable powder. | |
| 2. | Phosphonic Acid, [[(cyano-methyl)(phenylsulfinyl)amino] methyl]-, diphenyl ester | 30 parts |
| | Tween 65 | 3 parts |
| | Dodecylphenylpolyoxyethylene (5) ether | 1.5 parts |
| | Light mineral oil | 65.5 parts |
| | The components are blended and ground using a media mill to give an emulsifiable flowable. | |
| 3. | Phosphonic acid, [[(cyano-methyl)(phenylsulfinyl) amino]methyl]-, Bis(2-methoxyphenyl)ester | 20 parts |
| | Isopropylammonium dodecylbenzene sulfonate | 3 parts |
| | Nonylphenylpolyoxyethylene ether | 4 parts |
| | Castor oil polyoxyethylene ether | 2 parts |
| | 1,1,-Trichloroethane | 71 parts |
| | In applying the herbicides above on spray solutions it may be desirable to add additional surfactant such as Tween 20, nonyl phenylpolyoxyethylene ether, ethoxylate soya amine and the like to the tank to obtain maximum phytotoxicity. | |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G, Southern Weed Science Society, 33rd Annual Meeting Proceedings, Jan. 15–17, 1980; Auburn University Printing Service, Auburn, AL, U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator - Tool With A Future," Dale, James E., pp. 3–4, "The Recirculating Sprayer and Roundup® Herbicide," Derting, Claude W., pp. 5–7, and "C.D.A. Herbicide Application," McGarvey, Frank X., *Weeds Today,* Volume 11, Number 2, pp. 8–9, Late Spring, 1980, 309 W. Clark St., Champaign, IL, the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula 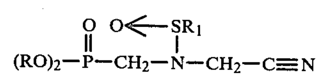 wherein R is selected from the group consisting of phenyl, naphthyl or biphenylyl; or phenyl, naphthyl or biphenylyl substituted with from 1 to 3 substituents independently selected from the group consisting of hydrogen, lower alkyl, lower alkoxy and methylenedioxy, and $R_1$ is phenyl or phenyl substituted with from 1 to 3 substituents selected from the group consisting of lower alkyl and lower alkoxy.

2. A compound according to claim 1 wherein R is phenyl or phenyl substituted with one lower alkyl or one lower alkoxy group.

3. A compound according to claim 2 wherein $R_1$ is phenyl or phenyl substituted with one substituent selected from the group consisting of lower alkyl and lower alkoxy.

4. A compound according to claim 3 wherein the compound is [[(cyanomethyl)(4-methylphenyl sulfinyl)-amino]methyl]phosphonic acid, diphenyl ester.

5. A compound according to claim 3 wherein the compound is [[(cyanomethyl)(phenyl sulfinyl)amino]-methyl]phosphonic acid, diphenyl ester.

6. A compound according to claim 2 wherein the compound is [[(cyanomethyl)(phenyl sulfinyl)amino]-methyl], phosphonic acid, bis(2-methoxyphenyl)ester.

* * * * *